United States Patent [19]

Metcalf et al.

[11] 4,041,041
[45] Aug. 9, 1977

[54] ACETYLENE DERIVATIVES OF AMINO ACIDS

[75] Inventors: Brian Walter Metcalf, Strasbourg; Michel Jung, Illkirch, both of France

[73] Assignee: Merrell Toraude et Compagnie, Strasbourg, France

[21] Appl. No.: 664,516

[22] Filed: Mar. 8, 1976

Related U.S. Application Data

[62] Division of Ser. No. 559,547, March 18, 1975, Pat. No. 3,959,356.

[51] Int. Cl.² .............. C07D 211/76; C07D 207/26; C07C 103/183; C07D 103/28
[52] U.S. Cl. .............. 260/293.86; 260/326.5 FL; 260/558 A; 260/559 A; 260/561 A; 424/267; 424/320
[58] Field of Search .............. 260/293.86, 326.5 FL, 260/558 A, 559 A, 561 A

[56] References Cited
U.S. PATENT DOCUMENTS

| | | | |
|---|---|---|---|
| 2,447,587 | 8/1948 | Martin et al. | 260/559 A |
| 2,460,708 | 2/1949 | Mozingo et al. | 260/482 R |
| 2,531,595 | 11/1950 | Albertson | 260/534 R |
| 2,588,969 | 3/1952 | Dickey et al. | 260/482 R |
| 2,649,438 | 8/1953 | Bruson | 260/293.86 |
| 3,223,729 | 12/1965 | Gubitz | 260/534 R |
| 3,959,356 | 6/1976 | Metcalf et al. | 260/293.86 |
| 3,960,927 | 6/1976 | Metcalf et al. | 260/293.86 |

Primary Examiner—John M. Ford
Attorney, Agent, or Firm—L. Ruth Hattan; Eugene O. Retter; George W. Rauchfuss, Jr.

[57] ABSTRACT

Novel compounds of the following general formula are useful pharmacologic agents:

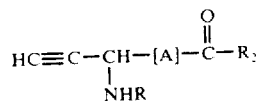

R is selected from hydrogen, alkylcarbonyl wherein the alkyl moiety contains from 1 to 4 carbon atoms, alkoxycarbonyl wherein the alkoxy moiety contains from 1 to 4 carbon atoms and may be straight or branched, and

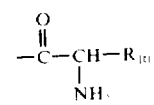

wherein $R_{10}$ is selected from hydrogen, a straight or branched lower alkyl group of from 1 to 4 carbon atoms, benzyl and p-hydroxybenzyl; $R_2$ is selected from hydroxy, a straight or branched alkoxy group of from 1 to 8 carbon atoms, a lower alkylamino group wherein the alkyl moiety contains from 1 to 5 carbon atoms, and

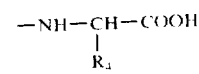

wherein $R_4$ is selected from hydrogen, a straight or branched lower alkyl group of from 1 to 4 carbon atoms, benzyl, and p-hydroxybenzyl; [A] is selected from

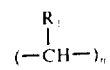

and —CH=CH— wherein $R_1$ is selected from hydrogen, lower alkyl of from 1 to 4 carbon atoms, phenyl and substituted phenyl wherein the substituents on the substituted phenyl may be attached at the ortho, meta or para positions of the phenyl ring and are selected from halogen, lower alkoxy of from 1 to 4 carbon atoms, and lower alkyl of from 1 to 4 carbon atoms; n is an integer of from 1 to 5; and the lactams of said compounds wherein [A] represents

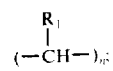

R and $R_1$ represent hydrogen and n is the integer 2 or 3; and pharmaceutically acceptable salts and individual optical isomers thereof.

6 Claims, No Drawings

ACETYLENE DERIVATIVES OF AMINO ACIDS

This is a division of application Ser. No. 559,547, filed Mar. 18, 1975, now U.S. Pat. No. 3,959,356, issued May 25, 1976.

BACKGROUND OF THE INVENTION

Several previous studies have shown that γ-aminobutyric acid is a major inhibitory transmitter of the central nervous system as reported, for example, by Y. Godin et al., Journal Neurochemistry, 16, 869 (1969) and that disturbance of the excitation and inhibition interplay can lead to diseased states such as Huntington's chorea (The Lancet, Nov. 9, 1974, pp. 1122–1123) Parkinsonism, schizophrenia, epilepsy, depression, hyperkinesis and manic depression disorders, Biochem. Pharmacol. 23, 2637–2649 (1974). Certain compounds are known to elevate brain levels of γ-aminobutyric acid, for example, n-dipropylacetate [Simler et al., Biochem. Pharm., 22, 1701 (1973)] by competitively inhibiting γ-aminobutyric acid transaminase resulting in a reversible effect which lasts for only about 2 hours. Also, 4-aminotetrolic acid [P. M. Beart el al., J. Neurochem. 19, 1849 (1972)] is known to be a competitive reversible inhibitor of γ-aminobutyric acid transaminase. We have now made the unexpected finding that compounds of our invention are able to irreversibly inhibit γ-aminobutyric acid transaminase and increase significantly the brain level of γ-aminobutyric acid in animals, rendering them useful in the treatment of the aforementioned diseased states. Furthermore, this increase is long lasting (over 24 hours) and, therefore, compounds of the present invention are not only stucturally novel but are quite different in their properties from known compounds which elevate brain levels of γ-aminobutyric acid only for a short period of time.

SUMMARY OF THE INVENTION

The compounds of the present invention may be represented by the following general Formula I:

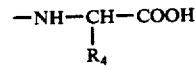

Formula I

R is selected from hydrogen, alkylcarbonyl wherein the alkyl moiety contains from 1 to 4 carbon atoms, alkoxycarbonyl wherein the alkoxy moiety contains from 1 to 4 carbon atoms and may be straight or branched, and

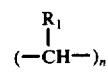

wherein $R_{10}$ is selected from hydrogen, a straight or branched lower alkyl group of from 1 to 4 carbon atoms, benzyl and γ-hydroxybenzyl; $R_2$ is selected from hydroxy, a straight or branched alkoxy group of from 1 to 8 carbon atoms, a lower alkylamino group wherein the alkyl moiety contains from 1 to 4 carbon atoms and

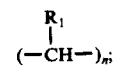

wherein $R_4$ is selected from hydrogen, a straight or branched lower alkyl group of from 1 to 4 carbon atoms, benzyl, and γ-hydroxybenzyl; [A] is selected from

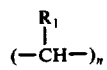

and —CH=CH— wherein $R_1$ is selected from hydrogen, lower alkyl of from 1 to 4 carbon atoms, phenyl and substituted phenyl wherein the substituents on the substituted phenyl may be attached at the ortho, meta and para positions of the phenyl ring and are selected from halogen, lower alkoxy of from 1 to 4 carbon atoms, and lower alkyl of from 1 to 4 carbon atoms; $n$ is an integer of from 1 to 5; and the lactams of said compounds wherein [A] represents

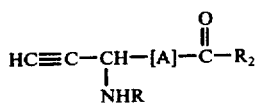

R and $R_1$ represent hydrogen and $n$ is the integer 2 or 3; and pharmaceutically acceptable salts and individual optical isomers thereof.

The compounds of general Formula I are useful as sedatives. The compounds of general Formula I wherein [A] represents —CH=CH— and

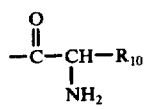

wherein $R_1$ is hydrogen, and $n$ is an integer of from 1 to 5, that is, compounds of the following general Formula II and the lactams of the compounds of Formula II wherein [A'] represents $(-CH_2-)_n$ and $n$ is the integer 2 or 3, as represented by Formula III, are useful as inhibitors of γ-aminobutyric acid transaminase resulting in an increase in brain levels of γ-aminobutyric acid rendering the compounds useful in the treatment of disorders of the central nervous system function consisting of involuntary movement associated with Huntington's chorea, Parkinsonism, extrapyramidal effects of drugs, for example, neuroleptics, seizure disorders associated with epilepsy, alcohol withdrawal, barbiturate withdrawal, psychoses associated with schizophrenia, depression, manic depression, and hyperkinesis. Compounds of this invention are also useful as hypothermic agents, myorelaxants, cholinergic agents, antibacterial agents, anticonvulsant agents, analgesics, anorexigenic agents, antiobesity agents, tranquilizers, sedatives and central nervous system stimulants.

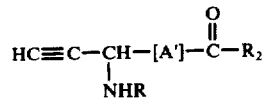

Formula II

In the above Formula II the substituent groups R and $R_2$ have the meanings defined in general Formula I, and [A'] is selected from —CH=CH— and $(-CH_2-)_n$ wherein n is an integer of from 1 to 5; and pharmaceutically acceptable salts and individual optical isomers;

Formula III

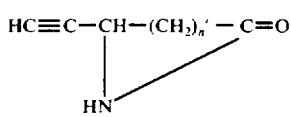

In the above Formula III $n'$ is the integer 2 or 3; and pharmaceutically acceptable salts and individual optical isomers thereof.

DETAILED DESCRIPTION OF INVENTION

As used herein, the term lower alkylcarbonyl means the substituent group

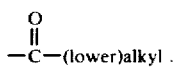

As used herein the term alkoxycarbonyl means the substituent group

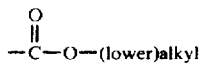

wherein the lower alkyl moiety may be straight or branched.

Illustrative examples of straight chain lower alkyl groups of from 1 to 4 carbon atoms referred to herein are methyl, ethyl, n-propyl and n-butyl, and of branched chain lower alkyl groups of from 1 to 4 carbon atoms are isopropyl, isobutyl, and tert-butyl.

Illustrative examples of straight chain lower alkoxy groups of from 1 to 4 carbon atoms as used herein are methoxy, ethoxy, n-propoxy and n-butoxy, and of branched chain lower alkoxy groups of from 1 to 4 carbon atoms are isopropoxy, isobutoxy, and tert-butoxy.

Illustrative examples of straight or branched alkoxy groups of from 1 to 8 carbon atoms as used herein are methoxy, ethoxy, n-propoxy, isopropoxy, n-butoxy, tert-butoxy, neopentoxy, pentoxy, octyloxy, heptyloxy and hexyloxy.

Illustrative examples of lower alkylamino groups which $R_2$ may represent are methylamino, ethylamino, n-propylamino and n-butylamino.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids such as methane sulfonic, salicyclic, maleic, malonic, tartaric, citric and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum; organic amines such as primary, secondary or tertiary amines, for example, cyclohexylamine, ethylamine, pyridine, methylaminoethanol, ethanolamine, and piperazine. The salts can be prepared by conventional means.

The compounds of this invention wherein [A] represents the group

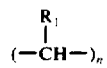

can be represented by the following Formula IV:

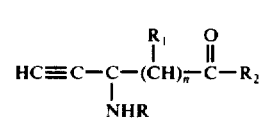

Formula IV wherein the substituents R, $R_1$, $R_2$ and n have the meanings defined in general Formula I.

The compounds of this invention wherein [A] represents —CH=CH— can be represented by the following Formula V:

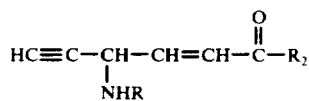

Formula V wherein the substituents R and $R_2$ have the meanings defined in general Formula I.

The lactams which are included within the scope of this invention are represented by the compounds of general Formula III, described hereinabove.

Illustrative examples of compounds of this invention are the following:

3-amino-4-yne-pentanoic acid,
4-amino-5-yne-hexanoic acid,
7-amino-8-yne-nonanoic acid,
6-amino-3-ethyl-7-yne-octanoic acid,
4-amino-2-(p-anisyl)-5-yne-hexanoic acid.
5-amino-3-(p-anisyl)-6-yne-heptanoic acid,
N-methyl-(2-amino-3-yne-butan-1-yl)carboxamide,
4-amino-3-phenyl-5-yne-hexanoic acid,
4-amino-5-yne-1-oxo-hexan-1-ylaminoacetic acid,
5-methoxycarbonylamino-6-yne-heptanoic acid,
3-amino-4-yne-pentanoic acid methyl ester,
4-amino-2-ene-5-yne-hexanoic acid,
4-acetylamino-5-yne-hexanoic acid Preferred compounds of this invention are those of general Formula II. More preferred compounds of this invention are those of general Formula II wherein the substituent group $R_2$ is hydroxy or alkoxy of from 1 to 8 carbon atoms. Still more preferred compounds of this invention are those of general Formula II wherein the substituent group $R_2$ is hydroxy, and n is the integer 1 or 2. An even more preferred group of compounds of this invention are those of general Formula II wherein the substituent group $R_2$ is hydroxy, n is an integer of 1 or 2 and R is hydrogen. Of the preferred compounds of this invention, the (+) isomers are the most preferred compounds.

The compounds of this invention have a variety of pharmacological utilities. The compounds of this invention are useful as sedatives. The compounds of general Formula II are useful as inhibitors of γ-aminobutyric acid transaminase resulting in an increase in brain levels of γ-aminobutyric acid rendering the compounds useful in the treatment of disorders of the central nervous system function consisting of involuntary movement associated with Huntington's chorea, Parkinsonism, extrapyramidal effects of drugs, for example, neuroleptics, seizure disorders associated with epilepsy, alcohol withdrawal, and barbiturate withdrawal, psychoses associated with schizophrenia, depression and manic depression and hyperkinesis. Compounds of this invention are also useful as hypothermic agents, myorelaxants, cholinergic agents, antibacterial agents, anticonvulsant agents, analgesics, anorexigenic agents, antiobesity agents, tranquilizers, sedatives, and central nervous system stimulants.

The sedative properties of the compounds of this invention were determined by measuring spontaneous motor activity in rodents by the procedure described by P. Dews, Brit. J. Pharmacol. 8, 46 (1953). For example administration of between 100–200 mg/kg (milligrams per kilogram) of the compound 4-amino-5-yne-hexanoic acid by either the intravenous, intraperitoneal or oral route to mice or rats produces a substantially decreased motor activity which appears 1 hour after administration of the compound and is still observable 48 hours after administration.

The ability of the compounds of general Formulas II and III to inhibit γ-aminobutyric acid transaminase is determined by in vitro and in vivo measure of γ-aminobutyric acid transaminase activity. γ-Aminobutyric acid levels are markedly increased in mice and rat brains after treatment with compounds of general Formula II at doses between 25–200 mg/kg by parenteral and oral routes. This ability is further shown by the protective effect of this treatment on audiogenic seizures in mice of the DBA strain measured by the general method described by Simler et al., Biochem. Pharmacol. 22, 1701 (1973), which is currently used to evidence anti-epileptic activity. For example administration between 50–200 mg/kg of 4-amino-5-yne-hexanoic acid to mice of the DBA strain which are susceptible to audiogenic seizures resulted in complete protection one hour after treatment, such protection lasting for over 16 hours.

The ability of the compounds of this invention at doses ranging from 50 to 200 mg/kg, to alleviate reserpine ptosis has been shown by the classical test of B. Rubin et al., J. Pharmacol. 120, 125 (1957), which is currently used to determine anti-depressant activity. For instance, in intraperitoneal injection of 50 mg/kg of 4-amino-5-yne-hexanoic acid in mice, one hour after an intravenous injection of 2 mg/kg reserpine dissolved in 2% ascorbic acid/water results in a palpebral aperture of 5.5, 3 hours after drug administration as compared to 6.5 for control reserpinized animals.

The ability of the compounds of this invention to promote loss of body weight in rats has been demonstrated by weighing animals which are given daily doses ranging from 10–50 mg/kg of these compounds. For instance, rats weighing 190 g, when given for four days, oral doses of 25 mg/kg 4-amino-5-yne-hexanoic acid (which is not a sedative dose) weigh only 170 gms as compared to 250 g for animals of the same group which are given saline for the same period.

The compounds of this invention can be administered orally or parenterally to animals, particularly warm blooded animals and mammals and humans either alone or in the form of pharmaceutical preparation containing as the active ingredient compounds of this invention to achieve the desired effect. Pharmaceutical preparations containing compounds of this invention and conventional pharmaceutical carriers can be employed in unit dosage forms such as solids, for example, tablets, pills, and capsules or liquid solutions, suspensions or elixirs for oral administration or liquid solution, suspensions and emulsions for parenteral use. The quantity of compounds administered can vary over a wide range to provide from about 0.1 mg/kg to about 300 mg/kg of body weight of the patient per day. Unit doses of these compounds can contain, for example from about 50 mg to 2000 mg of the compounds and may be administered, for example, from 1 to 4 times daily. Following are illustrative examples of pharmaceutical preparations containing the compounds of this invention:

|  | Per Tablet |
|---|---|
| (a) 3-amino-4-yne-pentanoic acid | 100.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

An illustrative composition for a parenteral injection is the following, wherein the quantities are on a weight to volume basis:

|  | Amount |
|---|---|
| (a) (+)4-amino-5-yne-hexanoic acid | 100.0 mg |
| (b) sodium chloride | q.s. |
| (c) water for injection to make | 20 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

An illustrative composition for hard gelatin capsules is as follows:

|  | Amount |
|---|---|
| (a) 3-amino-4-yne-pentanoic acid | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

The compounds of general Formula I wherein R is hydrogen, and R$_2$ is other than

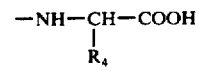

are prepared by reacting a suitably protected propargylamine derivative, as represented by compound I below, with an alkylating reagent in the presence of a base and subsequently unmasking the protected groups by treatment with acid or base as represented by the following reaction:

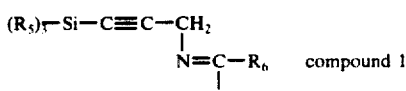

compound 1

BASE

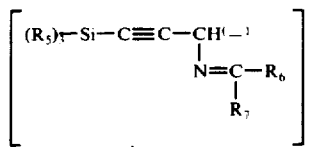

1. alkylating reagent
2. acid or base

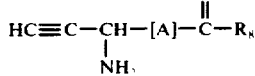

Formula VI

In the above reaction sequence, [A] has the meaning defined in general Formula I; $R_8$ is selected from hydroxy, a straight or branched lower alkoxy of from 1 to 8 carbon atoms and a lower alkylamino group wherein the alkyl moiety contains from 1 to 4 carbon atoms; $R_5$ is selected from a lower alkyl group having from 1 to 4 carbon atoms, such as methyl, ethyl and n-propyl; $R_6$ is selected from hydrogen and phenyl; and $R_7$ is selected from phenyl, tert-butyl and triethylmethyl.

In the above reaction, the protected propargylamine derivative compound I, is treated with a strong base to form a carbanion intermediate. Suitable strong bases are those which will abstract a proton from the carbon adjacent to the acetylene moiety, such as, alkyl lithium, for example, butyl lithium, or phenyl lithium, lithium di-alkylamide, for example, lithium diisopropylamide, lithium amide, tertiary potassium butylate, sodium amide and sodium hydroxide.

Following addition of the base, the alkylating reagent is added. The alkylating reagents employed in the above reaction are selected from derivatives having the structures:

(A) when [A] is —(CH)$_n$— and n is equal to 2,

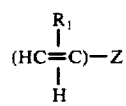

(B) when [A] is —(CH)$_n$— and n is equal to 1 or 3 to 5,

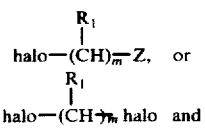

(C) when [A] is —CH=CH—, haloCH=CHCOR₉, or

-continued

HC≡C—COR₉ wherein $R_1$ has the meaning defined in general Formula I; Z is selected from cyano or

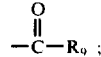

$R_9$ is selected from a straight or branched alkoxy group of from 1 to 8 carbon atoms; m is the integer 1 or 3 to 5; and halo is iodine or bromine.

When the alkylating reagent employed is the dihaloalkyl derivative as set forth in (B), subsequent to the alkylation reaction the ω-halogen is displaced with cyanide, and as when Z is cyano the reaction mixture is treated with an acid or base to hydrolyze the nitrile to the corresponding acid or amide derivative as represented by Formula VI by procedures well known in the art. Similarly, the protecting groups, that is, the acetylene and the amino protecting groups and the ester or amide functions, if desired, can be removed with aqueous acid, for example, hydrochloric or toluene sulfonic acid or aqueous base, for example, sodium hydroxide or potassium hydroxide. The protecting groups can also be removed by using hydrazine or phenylhydrazine.

The alkylation reaction is carried out in an aprotic solvent, for example, benzene, toluene, ethers, tetrahydrofuran, dimethysulfulfoxide, dimethyl formamide, dimethyl acetamide, hexamethyl phosphoramide and hexamethyl phosphortriamide. The reaction temperature varies from −120° C to about 25° C, and a preferred reaction temperature is about −70° C. The reaction time varies ½ hour to 24 hours. The protected propargylamine derivatives, compound I, are prepared by the addition of protecting groups on the acetylene function and the nitrogen function propargylamine. Protection of the nitrogen function of propargylamine is accomplished by forming in a known manner a Schiff's base with non-enolizable carbonyl bearing compound, such benzaldehyde, benzophenone, or trialkylacetaldehyde. Protection of the acetylenic function is accomplished by reacting the above described Schiff's base with trimethylsilychloride, triethylsilylchloride or higher trialkylsilylchloride forming in a known manner (E. J. Corey and H. A. Kirst, *Tetrahedron Letters*, 1968, 5041) the corresponding trialkylsilyl derivatives.

The alkylating reagents employed in the above reaction are known in the art or can be prepared by procedures well known in the art.

Compounds of this invention wherein R represents alkylcarbonyl are prepared from the corresponding acid wherein R represents hydrogen using the appropriate acid anhydride or halide of acetic acid, propionic acid, butyric acid or valeric acid. The amide derivatives can be isolated as the acid or a derivative thereof, for example, the ester by converting the acid to the acid halide, for example, by treating with thionyl chloride followed by alcoholysis, to give the appropriate ester by procedures generally known in the art.

Compounds of this invention wherein R represents alkoxycarbonyl are prepared from the corresponding acid wherein R represents hydrogen using an appropriate alkyl chloroformate, for example methyl chloroformate, ethyl chloroformate, n-propyl chloroformate, n-butylchloroformate, isobutyl chloroformate or tert-butyl chloroformate, in the presence of a base by procedures well known in the art.

Compounds of general Formula I wherein R is

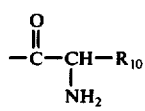

are prepared by treating an ester of a compound of Formula I, wherein R is hydrogen with a protected acid of the formula

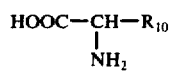

wherein the amino function is protected with a suitable blocking group, such as, benzyloxycarbonyl or tert-butoxycarbonyl. Either the free acid or a reactive derivative thereof, for example, an acid anhydride may be employed. When the free acid is used, and dehydrating agent such as N, N'-dicyclohexylcarbodiimide is used. The substituent $R_{10}$ has the meaning defined in general Formula I.

Compounds of this invention wherein $R_2$ represents

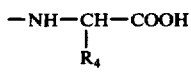

are prepared from the corresponding acid derivative wherein the amino function is protected with a suitable blocking group, such as, benzyloxycarbonyl or tert-butyoxycarbonyl. The amino protected derivatives either as the free acid, in which case a dehydrating agent such as N, N'-dicyclohexylcarbodiimide is used, or a reactive derivative of the acid, such as, an acid anhydride, is reacted with a compound of the structure

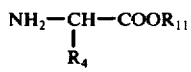

wherein $R_4$ has the meaning defined in general Formula I, and $R_{11}$ is a lower alkyl group, for example, methyl, or ethyl, followed by base hydrolysis to remove the protecting group by procedures well known in the art.

The lactams of this invention, as described by general Formula II, are prepared from the corresponding amino acid, that is a compound of the formula

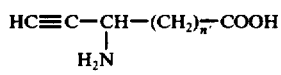

or ester thereof wherein n' is the integer 2 or 3, by procedures generally known in the art, for example, by treating the amino acid with a dehydrating agent such as dicyclohexlcarbodiimide or by heating the appropriate ester derivative.

The optical isomers of the compounds of this invention may be separated by a (+) or (−) binaphthylphosphoric acid derivative or salt of said derivative and an optically active base by the method described by R. Viterbo et al., in *Tetrahedron Letters* 48, 4617–4620 (1971) and in U.S. Pat. No. 3,848,030.

The following specific examples are illustrative of the compounds of this invention.

EXAMPLE 1

PROPAN-1-YNE-3-IMINOBENZYL

A solution of propargylamine (26.1 g, 0.47 M) and benzaldehyde (52 g, 49) in benzene (150 ml) is treated with $MgSO_4$ (20 g). The reaction mixture is stirred at room temperature for 30 minutes, then filtered. Excess water is removed by way of azeotropic distillation, the solution concentrated, and the residue distilled to give propan-1-yne-3-iminobenzyl (55.5g, 82%) b.p. 107°–110° C (10 mm Hg).

EXAMPLE 2

1-TRIMETHYLSILYL-1-PROPYNYL-3-IMINO-BENZYL

To a mechanically-stirred solution of propan-1-yne-3-iminobenzyl (43.5 g, 0.30 M) in tetrahydrofuran (400 ml) at 0° C is added, during 30 minutes, ethyl magnesium bromide (285 ml of a 1.12 M solution, 0.316 M). After 30 minutes at 0° C, the resulting solution is treated with a solution of trimethylsilylchloride (32.4 g, 0.30 M) in tetrahydrofuran (100 ml), the addition taking 45 minutes. After stirring at 0° C for an additional 1½ hours, the solution is treated with brine (8 × 100 ml), then dried and concentrated on a rotorvapor. The residue is distilled to afford a liquid (52.2 g, 80%) b.p. 92°–110° C, 0.6 mm Hg. An aliquot was redistilled to give 1-trimethylsilyl-1-propynl-3-iminobenzyl.

EXAMPLE 3

4-AMINO-5-YNE-HEXANOIC ACID

To 11.25 g (50 mM) of 1-trimethylsilyl-1-propynyl-3-iminobenzyl in 500 ml of tetrahydrofuran is added n-butyllithium (25 ml of a 2M solution, 50 mM) at −70° C. After 20 minutes at −70° C, freshly distilled methyl acrylate (4.3 g, 50 mM) is added. After 30 minutes at −70° C, 10 ml of water is added and the reaction mixture is allowed to come to room temperature. The tetrahydrofuran is then evaporated and concentrated HCl (20 ml) in water (150 ml) is added and the mixture heated at reflux overnight. On cooling, the aqueous solution is washed with methylene chloride, adjusted to a pH of 8 and reextracted with methylene chloride. The aqueous base is adjusted to a pH of 6. The product is isolated by ion exchange chromatography on an acid resin followed by recrystallization from ethanol-water.

EXAMPLE 4

3-AMINO-4-YNE-PENTANOIC ACID

In 250 ml of tetrahydrofuran is dissolved 3.8 g (17.5 mM) of 1-trimethylsilylpropan-1-yne-3-iminobenzyl and the solution is cooled at −78° C. To the solution, 9 ml of tetramethylethylenediamine and 9 ml of 2-molar n-butyllithium are added successively. After a few minutes, stirring 2.98 g (17.75mM) of ethylbromoacetate dissolved in 20 ml tetrahydrofuran is added. The reaction mixture is stirred for 5 minutes, cooling is stopped and 100 ml NaCl saturated water is added. The reaction mixture is extracted with ether and the organic phase is dried and concentrated and 6.5 g of an oily residue is obtained.

One-half of the above residue is dissolved in 30 ml tetrahydrofuran and 30 ml 6N HCl is added. The reaction mixture is refluxed overnight and the neutral components of the reaction mixture are extracted with methylenechloride in basic and acid conditions. The organic phase is evaporated to dryness and applied in a column of Amberlite I. R. 120 H. Fractions eluted with 1 N $NH_4OH$ are collected, evaporated to dryness and recrystallized from $EtOH/H_2$) 1:1 to give 50 mg of 3-amino-4-yne-pentanoic acid.

$C_5H_7NO_2$ Calculated: C: 53.08: H: 6.25 N: 12.38:
Found: C: 53.23: H: 6.40: N: 12.9.
I. R. (film 32 cm$^{-1}$ (C CH);
2150 cm$^{-1}$ (C C, N$^+$H$_2$);
1570 cm$^{-1}$ (COO$^-$).

EXAMPLE 5

(−) 4-AMINO-5-YNE-HEXANOIC ACID AND (+) 4-AMINO-5-YNE-HEXANOIC ACID 300 mg of the racemic compound 4-amino-5-yne-hexanoic acid is dissolved in 5 ml of absolute methanol, and 900 mg of (+) binaphthylophasophoric acid (BNPA) is added. After the solution is almost clear and an eventual solid residue has been filtered off, the solvent is evaporated and the dry residue dissolved at about 80° C in $EtOH/H_2O$ 1:1. On cooling, 440 mg of the crystallized enantiomer A is collected. The mother liquor is treated with HCl 1/N to pH 1 and filtered. The pH of the filtrate is adjusted to 6 and filtered through a column of Amberlite I. R. 120. The amino acid is eluted with 1M $NH_4OH$. After evaporation to dryness, the residue is recrystallized in $EtOH/H_2O$ 9:1 and 40 mg of (−) 4-amino-5-yne hexanoic acid is obtained: $(\alpha)_D^{20} = -29$ ($H_2O$ C: 1.33).

The 440 of an enantiomer A are processed in the same way as the corresponding mother liquor. After recrystallization in ethanol water (9:1), 30 mg of (+) 4-amino-4-yne-hexanoic acid are obtained $[\alpha]_D^{20} = +30$ ($H_2O$ C = 1.05).

EXAMPLE 6

4-ACETAMIDO-5-YNE-HEXANOIC ACID METHYL ESTER

A suspension of 1.27 g (10 mM) of 4-amino--yne-hexanoic acid in 25 ml of acetic anhydride in 10 ml of water is heated in an oil bath for 1 hour. The acetic anhydride is evaporated under vacuum, the residual syrup taken up in chloroform, and the solution is evaporated to dryness. This process is repeated several times to remove the acetic acid. The syrup is dissolved in 10 ml of chloroform, the solution cooled in ice water and under moisture exclusion 0.9 ml of thionyl chloride is added. The solution is stirred in the cold for 30 minutes and 2 ml of methanol is added while the cooling bath is removed. Stirring is continued for 1 hour. The evaporation of the solvent yields the product as an oil.

EXAMPLE 7

5-AMINO-6-YNE-HEPTANOIC ACID

To 1-trimethylsilyl-1-propynyl-3-iminobenzyl (10 mM) in 200 ml of tetrahydrofuran at −70° C was added n-butyllithium (10 mM) followed by 4-iodobutanoic acid methyl ester (10 mM) in 200 ml of tetrahydrofuran. The temperature was allowed to rise to −20° C and maintained at this temperature for 10 hours. The reaction product was extracted into ether to afford an oil. This oil was hydrolized in acid in the same manner as described in Example 3. The product is isolated by ion exchange chromotography and purified by recrystallization from ethanol-water.

Alternatively, 5-amino-6-yne-heptanoic acid may be prepared by the following procedure.

1-Trimethylsilyl-1-propynyl-3-iminobenzyl (10 mM) in 200 ml of tetrahydrofuran at −70° C was treated with n-butyllithium (10 mM), then 1-iodo-3-chloropropane (10 mM) in 10 ml of tetrahydrofuran. After 10 hours at −70° C, the tetrahydrofuran was removed by evaporation at room temperature, and replaced by 20 ml of dimethylformamide. To the reaction mixture were added sodium iodide (10 mM) and sodium cyanide (20 mM), and the solution was maintained at 50° C overnight. On cooling, the mixture was poured onto 300 ml of water and extracted with ether. The ether solution was washed with water, dried over magnesium sulfate and concentrated. The resulting oil was treated with HCl (6 N, 200 ml) and refluxed for 24 hours. On cooling, the mixture was extracted with methylene chloride, the aqueous base was adjusted to pH 9 using sodium carbonate and washed again with methylene chloride. The aqueous base was concentrated to about 50 ml, adjusted to pH of 5, and the product isolated by ion exchange chromotography and purified by recrystallization from ethanol-water.

EXAMPLE 8

4-AMINO-3-PHENYL-5-YNE-HEXANOIC ACID HYDROCHLORIDE

To a solution of 2:15 g of 1-trimethylsilyl-1-propynyl-3-iminobenzyl (10 mM) in 250 ml of tetrahydrofuran cooled to −78° is added 10 m moles of n-butyllithium. After 10 to 15 minutes, a solution of 1.65 of trans-cinnamic acid methyl ester (10 mM) is added. The solution is stirred at −78° C for 45 minutes and treated with brine. The product of the reaction is extracted by ether. The solution is dried over magnesium sulfate and evaporated to dryness leaving an oil which is treated with 6 NHCl for 24 hours. Upon evaporation to dryness, the remaining syrup is dissolved in water. The product is isolated by ion exchange chromotography on an acid resin and purified by recrystallization from ethanol-ether.

EXAMPLE 9

4-AMINO-5-YNE-2-ENE-HEXANOIC ACID

1-Trimethylsilyl-1-propynyl-3 iminobenzyl (10 mM) in 100 ml of tetrahydrofuran at −70° C was treated with n-butyllithium (10 mM). To the reaction mixture was added 2yne-propionic acid methyl ester (10 mM) in 10 ml of tetrahydrofuran. After 20 minutes at −70° C, 10 ml of water was added. On warming to room temperature, 6 NHCl (100 ml) was added and the mixture was refluxed overnight. On cooling, the aqueous solution was washed with methylene chloride, adjusted to a pH of 8 and reextracted with methylene chloride. The aqueous base was adjusted to a pH of 6. The product was isolated by ion exchange chromotography on an acid resin and purified by recrystallization from methanol-water.

Alternatively, 4-amino-5-yne-2-ene-hexanoic acid may be prepared by the following process.

1-Trimethylsilyl-1-propynyl-3-iminobenzyl (10 mM) in 100 ml of tetrahydrofuran at −70° C was treated with n-butyllithium (10 mM). To the reaction mixture was added methyl trans-3-chloroacrylate (10 mM) in 10 ml of tetrahydrofuran. After 1 hour at −70° C, 10 ml of water was added. On warming to room temperature, 6 NHCl (100 ml) was added and the mixture was refluxed overnight. The product was isolated in the same manner as described above.

EXAMPLE 10

4-(2-AMINOPROPRIONAMIDO)-5-YNE-HEXANOIC ACID

4-Amino-5-yne-hexanoic acid methyl ester is prepared by refluxing a suspension of 1.27 of 4-amino-5-yne-hexanoic acid in 20 ml of methanol with continuous anhydrous HCl bubbling through the reaction mixture for 3 hours followed by evaporation of the solvent, dissolution in water, neutralization with aqueous NaOH in the cold and ether extraction. The ether solution is dried over magnesium sulfate, filtered, and cooled to 0° C. Under moisture exclusion and solution of 10 mMoles of α-alanine wherein the amino function is protected with benzyloxycarbonyl and the acid function is activated with ethoxycarbonyl, prepared by the methods known in the art, in ether is added slowly with stirring. When addition is complete, the cooling bath is removed and stirring continued overnight. The solution is evaporated, leaving a syrupy residue which is taken up in 2 ml of methanol and 10 ml of 2 N aqueous ammonia added. The suspension is stirred at 50° C for 1 day, than extracted with ether. The product is isolated by ion exchange chromotography on an acid resin.

EXAMPLE 11

N-(2-PROPIONIC ACID)-3-AMINO-4-YNE-PENTAN-1YL CARBOXAMIDE

To a solution of 1.27 g of 4-amino-5-yne-hexanoic acid (10 mM) in 10 ml of water was added 10.0 ml of 2N NaOH. this solution was cooled in ice water and 1.87 g (11 mM) of benzylchloroformate was added slowly with stirring. When the addition was complete, stirring was continued for 1 hour. The solution is acidified to a pH of 4 by addition of aqueous HCl and the oily precipitate is extracted into ether. The ether solution is dried over magnesium sulfate, filtered and cooled. After addition 700 mg of triethylamine, an ethereal solution of 11 g of freshly distilled ethylchloroformate is added slowly over 1 hour with stirring. The precipitate is filtered off and to the ether solution a solution of alanine methyl ester in ether is added at once. The solution is kept overnight and then evaporated to dryness. The residue is taken up in 2 ml of methanol and 20 ml of 2 N aqueous NaOH is added. The suspension is stirred for 1 day at 50° C, then the solution is extracted with ether and adjusted to a pH of 7. The product is isolated by ion exchange chromotography on an acid resin.

We claim:

1. A compound of the formula

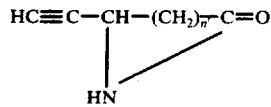

wherein $n'$ is the integer 2 or 3; or a pharmaceutically useful salt and individual optical isomers thereof.

2. A compound of the formula:

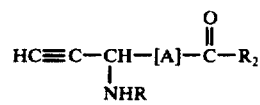

wherein R is hydrogen, alkylcarbonyl wherein the alkyl moiety contains from 1 to 4 carbon atoms, or

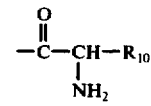

wherein $R_{10}$ is hydrogen, a straight or branched lower alkyl group of from 1 to 4 carbon atoms, benzyl or $p$-hydroxybenzyl; $R_2$ is a lower alkylamino group wherein the alkyl moiety has from 1 to 4 carbon atoms; [A] is —CH=CH— or

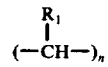

wherein $R_1$ is hydrogen, lower alkyl of from 1 to 4 carbon atoms, phenyl or substituted phenyl wherein the substituents on the substituted phenyl may be attached at the ortho, meta or para positions of the phenyl ring and are halogen, lower alkoxy of from 1 to 4 carbon atoms or lower alkyl of from 1 to 4 carbon atoms; $n$ is an interger of from 1 to 5; and the lactams of said compounds wherein [A] represents

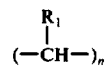

wherein $R_1$ represents hydrogen, and $n$ is the integer 2 or 3; or a pharmaceutically acceptable salt and individual optical isomers thereof.

3. A compound of claim 2 of the formula:

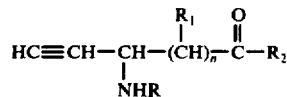

wherein R, $R_1$, $R_2$ and $n$ have the meanings defined in claim 2.

4. A compound of claim 3 wherein $n$ is the integer 1 or 2.

5. A compound of claim 4 wherein R is hydrogen.

6. A compound of claim 2 of the formula:

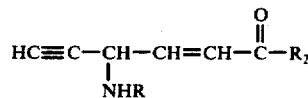

wherein R and $R_2$ have the meanings defined in claim 2.

* * * * *